(12) United States Patent
Sickenberger et al.

(10) Patent No.: US 7,277,829 B1
(45) Date of Patent: Oct. 2, 2007

(54) SYNTHETIC SIGNAL GENERATOR FOR TESTING BIOLOGICAL AEROSOL DETECTOR PEAK DETECTION ALGORITHMS

(75) Inventors: David W. Sickenberger, Bel Air, MD (US); Jerry B. Cabalo, Towson, MD (US); Richard Sickenberger, Bel Air, MD (US)

(73) Assignee: United States of America as represented by the Secretary of the Army, Washington, DC (US)

( * ) Notice: Subject to any disclaimer, the term of this patent is extended or adjusted under 35 U.S.C. 154(b) by 54 days.

(21) Appl. No.: 11/268,417

(22) Filed: Nov. 3, 2005

Related U.S. Application Data

(60) Provisional application No. 60/659,119, filed on Mar. 7, 2005.

(51) Int. Cl.
*G06F 15/00* (2006.01)
(52) U.S. Cl. .......................... 702/189; 702/22; 702/32; 422/50; 422/52; 422/55
(58) Field of Classification Search .............. 702/189, 702/127, 32, 22; 422/50, 52, 55
See application file for complete search history.

(56) References Cited

U.S. PATENT DOCUMENTS 6,692,696 B1 * 2/2004 Alberte ..................... 422/50

OTHER PUBLICATIONS

Medhi Benna et al., Generation of 3-D synthetic data for modeling of the CONSERT experiment (The radiotomgraphy of comet 67P/Churyumov-Gerasimenko), IEEE, vol. 52, No. 3, Mar. 2004, pp. 709-716.*
Robert w. Lowdermilk et al., Signal condition and data collection in synthetic instruments, IEEE, Jul. 2003, pp. 426-431.*

* cited by examiner

*Primary Examiner*—John Barlow
*Assistant Examiner*—Hien Vo
(74) *Attorney, Agent, or Firm*—Ulysses John Biffoni

(57) ABSTRACT

A method for generating a synthetic data signal is described. A synthetic data signal having any desired duration is generated from a data signal and a background signal of shorter duration. The duration of the background signal is extended by sampling the background signal at random times and for random durations. The sampled background signal is used to extend the background signal. Event data is identified from the data signal. The extended background signal is randomly populated with event data randomly sampled from the data signal to generate the synthetic data signal.

10 Claims, 1 Drawing Sheet

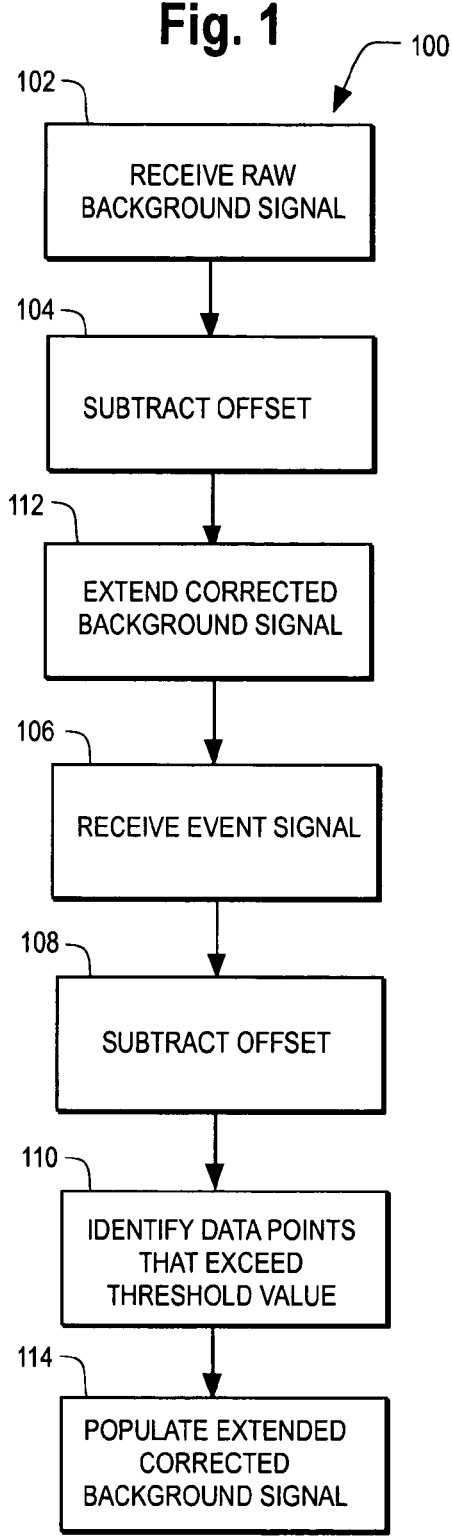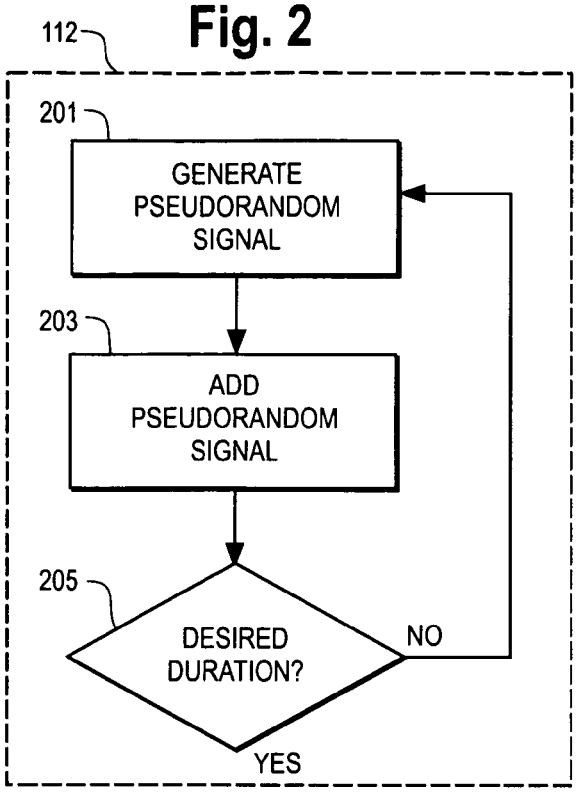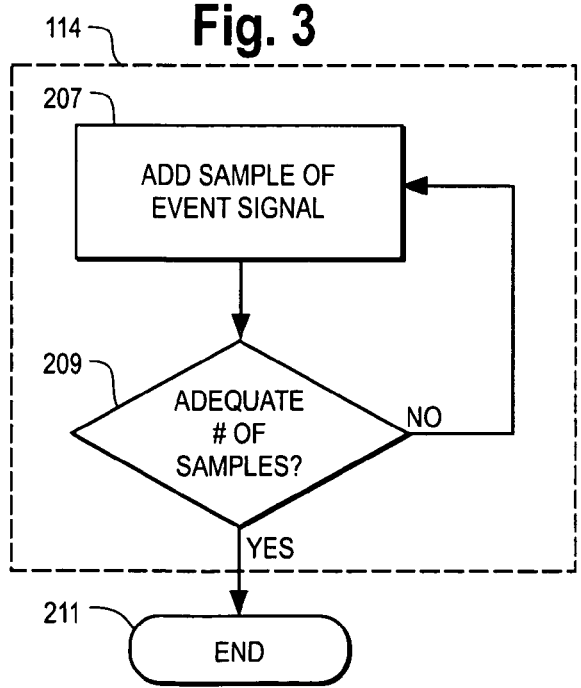

SYNTHETIC SIGNAL GENERATOR FOR TESTING BIOLOGICAL AEROSOL DETECTOR PEAK DETECTION ALGORITHMS

RELATED APPLICATIONS

Applicant claims the benefit under 35 U.S.C. § 119(e) of provisional application Ser. No. 60/659,119 filed Mar. 7, 2005.

GOVERNMENTAL INTEREST

The invention described herein may be manufactured, used and licensed by or for the U.S. Government.

TECHNICAL FIELD

This document relates to the generation of synthetic data.

BACKGROUND

Biological aerosol detectors are used to detect the presence of biological molecules in aerosol samples. The detectors are typically placed in locations where the potential for a chemical attack or industrial accident exists. Prior to placing the detectors in the field, it is desirable to test and characterize their responsiveness to expected signal events under operating conditions, including the responsiveness of any software that is used to operate the detector.

Under operating conditions, biological aerosol detectors can be expected to continuously collect data for long periods of time, such as weeks, months or years. The data is expected to consist largely of background signals and events and to reflect the absence of signal events that indicate the presence of biological molecules. To be effective under such operating conditions, biological aerosol detectors must be able to accurately and efficiently detect biological molecules in an aerosol sample even when the molecules are only present for a relatively short periods of time within much longer observation periods.

Biological aerosol detectors typically detect the presence of biological molecules using some form of peak detection algorithm. Peak detection algorithms, as their names imply, detect peaks in a data stream that rise above a background signal level, and that are indicative of signal events. To test the accuracy and efficiency of peak detection algorithms, the algorithms must be run on large samples of realistic looking data. Often, it is impractical to spend the weeks, months, or even years needed to collecting the amount of data that is needed to optimize and accurately test peak detection algorithms. Consequently, a method is needed for generating a synthetic signal that in a short period of time, accurately reflects the characteristics of the actual data signal the biological aerosol detector is expected to collect over a longer time period.

SUMMARY

A method of generating a synthetic data signal is provided. The method involves receiving a first signal indicative of background data, and a second signal indicative of event data. A pseudorandom signal is generated by sampling the first signal at a random location and for a random duration of time. The pseudorandom signal is added onto an end of the first signal to extend its duration, thereby generating an extended background signal. At least one sample of the second signal is added to the extended background signal at a random location to generate the synthetic data signal.

Aspects of the invention may include one or more of the following. A raw background signal may include a mean offset signal that is subtracted from the raw background signal to generate the first signal. A raw event signal may also include a mean offset signal that is subtracted from the raw event signal to generate the second signal. The sample of the second signal can be obtained by isolating at least one data point cluster, where a data point cluster is a plurality of successive data points that exceed a threshold value. The values of data points in the data point cluster may be scaled by a pre-selected factor before they are added to the background signal to generate the synthetic data signal.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a flowchart of a method for generating a synthetic data signal according to an embodiment of the present invention; and FIG. 2 is a more detailed representation of a portion of the method shown in FIG. 1.

FIG. 3 is a more detailed representation of a portion of the method shown in FIG. 1

Like reference symbols in the various drawings indicate like elements.

DETAILED DESCRIPTION

A method 100 for generating a synthetic data signal is shown in FIG. 1. At step 102 a signal indicative of a raw background signal is received. The raw background signal consists of data collected in the absence of a signal event. For example, in the context of biological aerosol detectors, the raw background signal consists of data collected during a period in which no biological molecules are detected in a sampled aerosol. If the raw background signal contains a mean offset value, it is subtracted at step 104 to generate a corrected background signal. The corrected background signal may have any duration, such as a few seconds or a few minutes. To generate a synthetic data signal of a desired length or duration, the corrected background signal is extended to that length at step 112, which is shown in greater detail in FIG. 2.

As shown in FIG. 2, the corrected background signal is extended by first generating a pseudorandom signal at step 201. The pseudorandom signal is generated by sampling the corrected background signal between a random start point and a random end point. At step 203, the generated pseudorandom signal is added to an end of the corrected background signal to extend the corrected background signal. At step 205, the length of the extended background signal is checked to determine it has the desired length, i.e., the length of the desired synthetic data signal. If the extended background signal does not have the desired length, steps 201 through 205 are repeated by generating and adding additional pseudorandom signals to the extended background signal until the extended background signal has the desired length.

Referring back again to FIG. 1, once the corrected background signal is extended to the length of the desired synthetic data signal, a raw event signal is received at step 106. The raw event signal contains data that indicates the occurrence of a signal event, such as the detection of a biological molecule in an aerosol sample. The raw event signal may include a mean offset value. If it does, the mean offset value is subtracted at step 108 to generate a corrected event signal.

At step 110, data points in the event signal or in the corrected event signal, as the case may be, and that are characteristic of a signal event, are identified. Signal events are typically characterized in that they contain one or more data points that exceed a threshold value. The threshold value can be user-selected, pre-selected or dynamically selected to efficiently detect a signal event while rejecting background data. When signal events are characterized by a single data point that exceeds a threshold value, all of the data points in the corrected event signal that exceed the threshold value are identified as signal events in step 110. When signal events are characterized by a cluster of successive data points each of which exceeds a threshold value, all such data point clusters are identified as signal events in step 110, and any non-clustered data points that exceed the threshold value are rejected as background events.

When all of the data points or data point clusters that characterize a signal event have been identified in step 110, they are used in step 114 to generate a synthetic data signal by populating the extended corrected background signal. This is shown in more detail in FIG. 3. At step 207, at least one data point or cluster of data points identified in step 110 (FIG. 1) is added to the extended corrected background signal, thereby generating the synthetic data signal. The added data point or data point cluster is randomly selected from those identified in the corrected event signal (step 110), and is added to the extended corrected background signal at a random point.

It should be noted here that for certain types of data, the value of the data point or data points that are identified in the corrected event signal at step 110 (FIG. 1) may indicate the type of signal event that was originally detected. For example, the value of one or more data points identified in step 110 as characteristic of a signal event in a biological aerosol detector will be proportional to the size of the biological molecule detected. When the value of data points identified in step 110 indicates the type of data detected, the value can be scaled before the data point is added to the extended corrected background signal at step 207. This allows data representing one type of detected signal event to simulate the data expected from different types of signal event. For example, by scaling the value of a data point identified in step 110 as a signal event from a biological aerosol detector, the data point can be used to simulate the data signal expected from detecting an arbitrarily sized biological molecule, regardless of the size of the biological molecule that was actually detected.

At step 209, a check is performed after each data point or data point cluster is added to the extended corrected background to determine whether the desired number of data points or data point clusters have been added. If not, steps 207 and 209 are repeated and other data points or data point clusters are added to the extended corrected background until the desired number of data points or data point clusters has been added. The total number of data point or data point clusters to be added to the extended corrected background signal can be determined by a user or by other means, and reflects the desired number of signal events or the density of signal events in the synthetic data signal. In general, the more data points or data point clusters added to the extended corrected background signal in steps 207 through 209, the greater the density of signal events in the synthetic data signal. When enough data points or data point clusters have been added at step 209, a synthetic data signal of the desired duration and signal event density has been generated.

The invention can be implemented in digital electronic circuitry, or in computer hardware, firmware, software, or in combinations of them. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

While a number of specific embodiments of the invention have been described, it will be understood that additional embodiments and various modifications may be made without departing from the spirit and scope of the invention. For example, the method is not restricted to any particular type of data, and can include analog or digital data. The method may be used to create synthetic data representing the operating characteristics of a receiver or signal detector, such as the operating characteristics of a biological aerosol detector or other optical detector. Other types of synthetic data can also be generated from a sample of background data and expected event data. The generated synthetic data can be used to test peak detection algorithms or other operating characteristics of a signal or event detector. In one embodiment, a synthetic data signal having a duration of weeks or months can be generated from a signal having a duration as short as a few seconds or minutes. While the steps of have been described in a particular order, the ordering of certain steps can be rearranged without departing from the spirit and scope of the invention. Depending on the nature of the data to be detected and simulated, identifying data corresponding to a signal event may include identifying data points that fall within a threshold range or below a threshold value. Accordingly, these and other embodiments of the invention fall within the scope of the following claims.

What is claimed is:

1. A method of generating a synthetic data signal for evaluating detector peak detection algorithms, comprising:

receiving a first signal indicative of a background signal;
receiving a second signal indicative of an event signal;
generating a pseudorandom signal from the first signal by sampling the first signal at a random location and for a random period of time;
generating an extended background signal by adding the pseudorandom signal onto an end of the first signal to extend the duration of the first signal;
adding at least one sample of the second signal to the extended background signal at a random location of the extended background signal to generate the synthetic data signal; and
testing said peak detection algorithms with said synthetic data signal.

2. The method of claim 1, wherein receiving a first signal comprises receiving a raw background signal and subtracting a mean offset from the raw background signal to generate the first signal.

3. The method of claim 1, wherein receiving a second signal comprises receiving a raw event signal and subtracting a mean offset from the raw event signal to generate the second signal.

4. The method of claim 1, wherein adding the at least one sample of the second signal comprises isolating clusters of successive data points in the second signal that each exceed a threshold value.

5. The method of claim 1, further comprising scaling the at least one sample of the second signal before adding it to the extended background signal to generate the synthetic signal.

6. A computer program product, implemented on a machine readable medium, comprising instructions operable to cause a programmable processor to:

receive a first signal indicative of a background signal;
receive a second signal indicative of an event signal;
generate a pseudorandom signal from the first signal by sampling the first signal at a random location and for a random period of time;
generate an extended background signal by adding the pseudorandom signal onto an end of the first signal to extend the duration of the first signal; and to
add at least one sample of the second signal to the extended background signal at a random location of the extended background signal to generate a synthetic data signal for testing detector peak detection algorithms.

7. The computer program product of claim 6, wherein the instruction to receive a first signal comprises instructions to receive a raw background signal and to subtract a mean offset from the raw background signal to generate the first signal.

8. The computer program product of claim 6, wherein the instruction to receive a second signal comprises instructions to receive a raw event signal and to subtract a mean offset from the raw event signal to generate the second signal.

9. The computer program product of claim 6, wherein the instruction to add the at least one sample of the second signal comprises instruction to isolate clusters of successive data points in the second signal that each exceed a threshold value.

10. The computer program product of claim 6, further comprising instructions to scale the at least one sample of the second signal before adding it to the extended background signal to generate the synthetic signal.

* * * * *